United States Patent [19]

Desmurs et al.

[11] Patent Number: 5,260,475
[45] Date of Patent: Nov. 9, 1993

[54] ESTERIFICATION OF HYDROXYBENZOIC ACIDS

[75] Inventors: Jean-Roger Desmurs, St. Symphorien D'ozon; Serge Ratton, Saint Germain En Laye, both of France

[73] Assignee: Rhone-Poulenc Chimie, Courbevoie, France

[21] Appl. No.: 719,467

[22] Filed: Jun. 24, 1991

[30] Foreign Application Priority Data

Jun. 22, 1990 [FR] France .................. 90 07818

[51] Int. Cl.⁵ .................. C07C 313/00; C07C 9/02
[52] U.S. Cl. .................. 560/61; 560/62; 560/65; 560/71; 560/72; 560/73; 560/75
[58] Field of Search .................. 560/61, 62, 65, 71, 560/72, 73, 75

[56] References Cited

U.S. PATENT DOCUMENTS 3,341,575  9/1967  Fierce et al. .................. 260/493

FOREIGN PATENT DOCUMENTS 0002872  7/1979  European Pat. Off. .
875999  8/1961  United Kingdom .

Primary Examiner—José G. Dees
Assistant Examiner—Porfirio Nazario
Attorney, Agent, or Firm—Burns, Doane, Swecker & Mathis

[57] ABSTRACT

The hydroxybenzoic acids, e.g., salicylic acid and para-hydroxybenzoic acid, are esterified by reacting same with a halocarbon, advantageously a halogenated derivative of an aliphatic, cycloaliphatic, cyclo- or arylaliphatic hydrocarbon, in essentially homogeneous liquid phase and in the presence of a nonquaternizable tertiary amine.

25 Claims, No Drawings

ESTERIFICATION OF HYDROXYBENZOIC ACIDS

CROSS-REFERENCE TO COMPANION APPLICATION

Our copending application Ser. No. 07/719,468, filed concurrently herewith and assigned to the assignee hereof.

BACKGROUND OF THE INVENTION

1. Field of the Invention

The present invention relates to the esterification of hydroxybenzoic acids, and, more especially, relates to the esterification of salicylic acid and parahydroxybenzoic acid.

2. Description of the Prior Art

One conventional technique in this art for preparing esters of hydroxybenzoic acids comprises reacting hydroxybenzoic acid with a halogenated compound, particularly an alkyl halide, in a biphasic medium in the presence of a strong base.

A major disadvantage of this procedure is that several secondary competing reactions are also carried out, resulting in a decrease in yield, particularly competing reactions between the esterification of the carboxyl function and the O-alkylation reaction of the hydroxy function borne by the aromatic ring.

This results in a reduction in the yield of the ester by virtue of the formation of by-products.

Moreover, the conditions of the reaction result in hydrolysis of the halide employed, forming an alcohol in the aqueous phase which necessarily must be subsequently removed. Therefore, a loss in the amount of such halide also ensues.

SUMMARY OF THE INVENTION

Accordingly, a major object of the present invention is the provision of an improved process for the esterification of hydroxybenzoic acids which avoids or conspicuously ameliorates the above disadvantages and drawbacks to date characterizing the state of the prior art.

By the term "hydroxybenzoic acid" is intended any aromatic compound bearing at least one hydroxy function and at least one carboxy function.

Briefly, the present invention features the esterification of hydroxybenzoic acid, comprising reacting such acid with a halogenated derivative of an aliphatic, cycloaliphatic, cyclo- or arylaliphatic hydrocarbon in essentially homogeneous liquid phase and in the presence of a nonquaternizable tertiary amine.

By the generic term "halogenated derivative" are intended the aforesaid halogenated compounds.

By the expression "nonquaternizable amine" is intended an amine which, when subjected to the conditions of reaction in the absence of the hydroxybenzoic acid substrate, is not quaternized by the halogenated derivatives or is quaternized to only a slight extent, corresponding to a transformation of the halogenated derivative to quaternized amine equal to not more than 10% and preferably ranging from 0% to 5%.

DETAILED DESCRIPTION OF THE PREFERRED EMBODIMENTS OF THE INVENTION

More particularly according to the present invention, the hydroxybenzoic acid and the halogenated derivative are reacted in essentially homogeneous liquid phase. This expression connotes that the different reactants are liquid under the reaction conditions, but the process does not exclude the presence of optionally solid catalysts.

The esterification reaction according to the invention can be carried out in the absence of a solvent or in the presence of an organic solvent. It is preferred to employ conditions that facilitate conducting the reaction in a homogeneous medium.

The process of the invention is applicable to all hydroxybenzoic acids and more particularly to those corresponding to the following Formula (I):

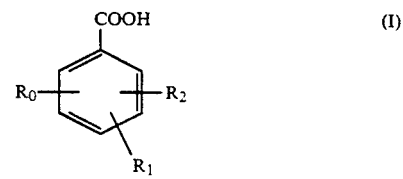

in which Formula (I) $R_o$ is a hydroxy group; $R_1$ and $R_2$, which may be identical or different, are each a hydrogen atom, an —OH group, a straight or branched $C_{1-6}$ alkyl radical, an alkoxy radical $R_3$—O—, wherein $R_3$ is a $C_{1-6}$ straight or branched alkyl radical, a —COOH group, a —CHO group, a $C_{2-6}$ acyl radical, a group —COOR'$_3$ wherein R'$_3$ is a straight or branched $C_{1-4}$ alkyl radical, an —NO$_2$ group, a halogen atom, preferably fluorine, chlorine or bromine, or a —CF$_3$ group.

Among the compounds of Formula (I), those in which $R_1$ and $R_2$, which may be identical or different, are each a hydrogen atom, a hydroxy group, or a straight or branched $C_{1-6}$ and preferably $C_{1-4}$ alkoxy radical are more particularly preferred.

More particularly preferred are those compounds of Formula (I) in which each of $R_1$ and $R_2$, which may be identical or different, is a hydrogen atom, a hydroxy group, a methyl radical or a methoxy radical.

Exemplary compounds of Formula (I) include:
2-Hydroxybenzoic acid (salicylic acid),
3-Hydroxybenzoic acid,
4-Hydroxybenzoic acid,
3-Methylsalicylic acid,
4-Methylsalicylic acid,
5-Methylsalicylic acid,
3-Hydroxy-4-methylbenzoic acid,
3-Methoxysalicylic acid,
4-Methoxysalicylic acid,
5-Methoxysalicylic acid,
3-Hydroxy-4-methoxybenzoic acid (isovanillic acid),
4-Hydroxy-3-methoxybenzoic acid (vanillic acid),
3-Hydroxy-4,5-dimethoxybenzoic acid,
4-Hydroxy-3,5-dimethoxybenzoic acid (syringic acid),
5-Hydroxyisophthalic acid,
3-Aminosalicylic acid,
4-Aminosalicylic acid,
5-Aminosalicylic acid,
3-Hydroxy-2-aminobenzoic acid,
3-Nitrosalicylic acid,
3-Hydroxy-4-nitrobenzoic acid,
4-Hydroxy-3-nitrobenzoic acid,
3-Hydroxy-4-methyl-2-nitrobenzoic acid,
3,5-Diiodosalicylic acid,
2,3-Dihydroxybenzoic acid,
2,4-Dihydroxybenzoic acid, 2,5-Dihydroxybenzoic acid,
2,6-Dihydroxybenzoic acid,
3,4-Dihydroxybenzoic acid (protocatechuic acid),
3,5-Dihydroxybenzoic acid,
3,5-Dihydroxy-4-methylbenzoic acid,
2,3,4-Trihydroxybenzoic acid,
2,4,6-Trihydroxybenzoic acid,
3,4,5-Trihydroxybenzoic acid.

The hydroxybenzoic acids are preferably salicylic acid and 4-hydroxybenzoic acid.

The process of the invention thus comprises contacting at least one of the above hydroxybenzoic acids with at least one halogenated derivative that can be represented by the Formula (II):

$$R_4-X \quad (II)$$

in which X is a halogen atom that is not in a vinylic or alkynylic position and $R_4$, which is optionally substituted, is an acyclic saturated or unsaturated straight or branched aliphatic radical, a cycloaliphatic saturated or unsaturated monocyclic or polycyclic radical; or a straight or branched saturated or unsaturated cyclo- or arylaliphatic radical.

The halogen atom can be chlorine, bromine or iodine, but the first two are the preferred.

The radical $R_4$ is preferably:

(1) a straight or branched alkyl, alkenyl, alkadienyl or alkynyl radical, preferably having 1 to 12 carbon atoms, with the hydrocarbon chain optionally being interrupted by one of the following groups:

$$-O-, -CO-, -COO-, -\underset{R_5}{N}-, -CO-\underset{R_5}{N}-$$

in which $R_5$ is a hydrogen atom or a $C_{1-4}$ alkyl radical or a cyclohexyl or phenyl radical, with the proviso that $R_5$ is a hydrogen atom in the event that the nitrogen atom is not quaternizable and/or bearing one of the following Y substituents: an —OH group, a —COOH group, a —CHO group, an —NO$_2$ group, a —C≡N group, a nonquaternizable or N-protected amine group, a halogen atom, preferably chlorine or bromine, or a —CF$_3$ group. Exemplary of the aliphatic radicals $R_4$ are methyl, ethyl, propyl, isopropyl, butyl, isobutyl, sec-butyl, t-butyl, 2-ethylbutyl, pentyl, isopentyl, neopentyl, t-pentyl, 2-methylpentyl, hexyl, 2-ethylhexyl, allyl, 3-methyl-2-butenyl, 3-hexenyl, methoxymethyl and acetamidomethyl;

(2) a cycloalkyl or cycloalkenyl radical preferably having 5 to 7 carbon atoms and optionally bearing one or more Y substituents such as those indicated above and/or one or more Z substituents which can be a $C_{1-4}$ straight or branched alkyl radical, a $C_{1-4}$ straight or branched alkoxy radical or a radical of the formulae:

$$R_5-CO-, R_5-COO-, R_5-O-CO-, R_5-\underset{R_5}{N}-$$

$$R_5-CO-\underset{R_5}{N}-, R_5-\underset{R_5}{N}-CO-$$

in which $R_5$ is as defined above; such radicals can be polycyclic and bridged. Exemplary of the cycloaliphatic radicals $R_4$ are the cyclohexyl radical and the cyclohex-1-en-yl radical;

(3) a saturated or unsaturated, straight or branched acyclic aliphatic radical such as those indicated under (1), bearing a cyclic substituent which comprises a saturated, unsaturated or aromatic carbocyclic or heterocyclic ring member.

The acyclic aliphatic radical can be linked to the ring by a valence bond or by one of the following groups:

$$-O-, -CO-, -COO-, -\underset{R_5}{N}-, -CO-\underset{R_5}{N}-$$

in which $R_5$ is as defined above.

Exemplary such ring members include:

(a) a saturated or unsaturated monocyclic or polycyclic cycloaliphatic radical such as those indicated under (2);

(b) a phenyl, tolyl or xylyl radical, optionally bearing one or more Y or Z substituents;

(c) a saturated, unsaturated or aromatic monocyclic heterocyclic radical containing, as hetero atoms, one or more atoms of oxygen, nitrogen or sulfur, and containing 4 to 6 atoms in the ring, such radical optionally bearing one or more Y or Z substituents. Exemplary such heterocylic radicals include pyrrolidinyl, imidazolidinyl, piperidyl, furyl, pyrrolyl, thienyl, isoxazolyl, furazanyl, isothiazolyl, imidazolyl, pyrazolyl, pyridyl, pyridazinyl and pyrimidinyl;

(d) a radical having a chain of 2 to 4 groups such as those indicated in paragraphs (a) and/or (b) and/or (c), bonded to each other by a valence bond and/or by one of the following groups:

$$-O-, -S-, -\underset{R_5}{N}-, -CO-\underset{R_5}{N}-, -CO-,$$

$$-COO-, -SO_2-, -N=N-, -N=N-, -\underset{\underset{O}{\Downarrow}}{P}-\underset{R_5'}{}$$

and/or at least one $C_{1-4}$ group of the alkylene or alkylidene type; in which formulae $R_5$ and $R_5'$ are each a hydrogen atom, a $C_{1-4}$ alkyl radical or a cyclohexyl or phenyl radical, with the proviso that $R_5$ can be a hydrogen atom in the event that the nitrogen atom does not quaternize. Particularly exemplary thereof are the biphenylyl, 1,1'-biphenylmethylene, 1,1'-biphenyloxy, 4-(4-carboxyphenoxy)-phenyl, 3,4-methylenedioxyphenyl, 2-acetylphenyl, 4-acetylphenyl, 2-benzoylphenyl, 4-benzoylphenyl, 3-benzoyloxy-2-ethylphenyl, 2-acetoxyphenyl, 4-acetoxyphenyl, 2-acetamidophenyl and 4-acetamidophenyl radicals;

(e) an aromatic radical containing 2 or 3 aromatic carbocyclic and/or heterocyclic rings and constituting an orthocondensed system.

The aromatic rings are preferably benzene and pyridine rings.

Exemplary polycyclic aromatic radicals include anthryl, quinolyl, naphthyridinyl, benzofuranyl, and inodolyl radicals.

Particularly exemplary cyclo- or arylaliphatic radicals $R_4$ bearing a cyclic substituent include the cyclohexylmethyl, cyclohexylbutyl, benzyl, 2- phenylethyl, 2-[4-(2-butyl)-phenyl]ethyl, styryl, alpha-phenylcyclohexylmethyl, phenoxymethyl, and phenoxyethyl radicals.

In the definition of the $R_4$ radical of the halogenated derivative of Formula (II), it should be noted that the latter can bear one or more Y or Z substituents. Typically, "one or more" does not exceed a total of 3.

In a preferred embodiment, the radical $R_4$ is a $C_{1-8}$ straight or branched alkyl radical, for example methyl, ethyl, propyl, isopropyl, butyl, isobutyl, sec-butyl, t-butyl, 2-ethylbutyl, pentyl, isopentyl, neopentyl, t-pentyl, 2-methylpentyl, hexyl or 2-ethylhexyl; a $C_{2-8}$ straight or branched alkenyl radical containing an ethylenic double bond that is beta to the X group, for example allyl, 3-methyl-2-butenyl or 3-hexenyl; a cyclohexyl radical optionally substituted by a straight or branched $C_{1-4}$ alkyl radical; an arylalkyl radical such as that represented by the following formula $-(CH_2)_m-Ph$ in which m is an integer ranging from 1 to 4, preferably 1, and Ph is phenyl.

Particularly exemplary halogenated derivatives corresponding to Formula (II) are methyl bromide, ethyl bromide, n-propyl bromide, bromoisopropane, bromohexane, bromoheptane, bromooctane, 1-bromo-2-methylbutane, 1-bromo-3-methylbutane, 2-bromo2-methylbutane, allyl bromide, allyl chloride, crotyl chloride, 3-chloro-2-methylpropene, 1-chloro-2-butene, 1-chloro-3-methyl-2-butene, prenyl bromide, geranyl bromide, geranyl chloride, bromocyclobutane, bromocyclopentane, bromocyclohexane, bromocycloheptane, (bromomethyl)cyclopropane, 2-(chloromethyl)pyridine, 3-(chloromethyl)pyridine, 4-(chloromethyl)pyridine, benzyl bromide, benzyl chloride, 4-chloromethylstilbene, 1-bromomethyl-naphthalene, 2-bromomethyl-naphthalene.

As regards the selection of the halide used, i.e., chloride or bromide, this is determined by the nature of the hydrocarbon from which the halide is formed, and the economic constraints.

A brominated compound can be used in all instances of carrying out the process of the invention. However, the chlorides are less expensive and thus are preferably used, but they are not always suitable. Indeed, it is not possible in accordance with the invention to use a halide of the chloride type when the hydrocarbon chain bearing the chlorine atom is unsaturated and such chlorine atom is in the beta position with respect thereto; however, such unsaturation can be present in an aliphatic chain or an aromatic ring. For example, benzyl chloride can advantageously be used.

In the above definition of the radical $R_4$, it is noted that $R_4$ can bear another halogen atom. Thus, the process of the invention can produce diesters of hydroxybenzoic acids. It will be appreciated that the halogen atoms must not be present on the same carbon atom.

Diesters of a hydroxybenzoic acid can be produced from dibrominated derivatives, whatever their nature, for example, dibromomethane, 1,2-dibromoethane, 1,2-dibromopropane, 1,3-dibromopropane, 1,2-dibromobutane, 1,3-dibromobutane, 1,4-dibromobutane, 1,6-dibromohexane, 1,4-dibromo-2-butene, 1,4-dibromobutyne and 1,4-bis-(bromomethyl)-benzene; dichlorinated derivatives unsaturated in the beta position with respect to the chlorine atoms, for example, 1,4-dichloro-2-pentene and 2,4-bis(chloromethyl)benzene; mixed brominated and chlorinated derivatives in the event of unsaturation in the beta position with respect to the chlorine atom. To the contrary, for example if bromochloroethane is used, it is not possible to produce a diester, but only a beta-chlorinated monoester.

In the process of the present invention, it is also possible to produce a diester in the event that one of the radicals $R_o$, $R_1$ and $R_2$ of the hydroxybenzoic acid of Formula (I) is a —COOH function.

The process of the present invention also requires the presence of a nonquaternizable tertiary amine. This serves to neutralize the hydrohalic acid liberated over the course of the esterification.

The amines used as catalysts in the present process are tertiary amines of which at least one of the radicals borne by the nitrogen atoms is a branched aliphatic radical and preferably where at least two of such radicals are branched aliphatic radicals.

Exemplary amines according to the invention are those corresponding to the following Formula (III):

in which R', R" and R'", which may be identical or different, are each a $C_{1-12}$ straight or branched saturated or unsaturated aliphatic radical, a $C_{5-7}$ saturated or unsaturated cycloaliphatic radical, or a phenyl radical; in said Formula (III), at least one of the radicals R', R" and R'" is a branched aliphatic radical, and at most one of the radicals R', R" and R'" is a phenyl radical.

Exemplary branched radicals are those aliphatic radicals branched on the carbon that is alpha with respect to the nitrogen atom.

Among the compounds of Formula (III), preferred are those wherein at least two of the radicals R', R" and R'" are branched aliphatic radicals, with the branching preferably being on the carbon alpha with respect to the nitrogen atom.

Exemplary such radicals R', R" and R'" are methyl, ethyl, propyl, isopropyl, butyl, isobutyl, sec-butyl, t-butyl, pentyl, isopentyl, neopentyl, t-pentyl, hexyl, isohexyl, octyl, isooctyl, decyl, dodecyl, cyclohexyl and phenyl radicals.

Exemplary tertiary amines suitable for use according to the invention include diisopropylmethylamine, N,N-diisopropylethylamine, N,N-diisopropyl-n-propylamine, N,N-diisopropylpropylamine, N,N-di(sec-butyl)ethylamine, N,N,N-triisopropylamine, N,N-diisopropylallylamine, N,N-di(sec-butyl)allylamine, N,N-dicyclohexylethylamine, N,N-diisopropylaminoethanol.

It is preferred to use a base having a pKa measured at 25° C. greater than or equal to 9.0, preferably greater than or equal to 10.

Preferably, N,N-diisopropylethylamine is used.

Moreover, it is preferred to use a nonquaternizable water-soluble tertiary amine, because this facilitates its recovery upon completion of the reaction and avoids parasitic reaction with the halogenated derivative.

In a preferred embodiment of the invention, an onium catalyst is introduced into the reaction medium to improve the reaction kinetics.

The onium compounds used in the process of the invention are those derived particularly from nitrogen, phosphorus, arsenic, sulfur, selenium, oxygen, carbon or iodine, and coordinated to hydrocarbon residues. The onium ions derived from nitrogen, phosphorus or arsenic are quadricoordinated, the onium ions derived from sulfur, selenium, oxygen, carbon and S=O are tricoordinated and the onium ions derived from iodine are dicoordinated.

The hydrocarbon residues coordinated to these different elements are alkyl, alkenyl, aryl, cycloalkyl or aralkyl radicals, optionally substituted, or 2 coordinated hydrocarbon radicals optionally joined to form a single bivalent radical.

The nature of the anions associated with the organic cations is not of critical importance. All strong or intermediate bases can be used as the anion. By "strong or intermediate base" is intended any anion corresponding to the classical definition of R. Pearson, in *Journal of Chem. Ed.* 45, pages 581–587 (1968); the terms "strong" and "intermediate" respectively having the meanings of the terms "hard" and "borderline" reported in this article.

Among the onium ions suitable for the process of the present invention, particularly preferred are those of the following general formulae:

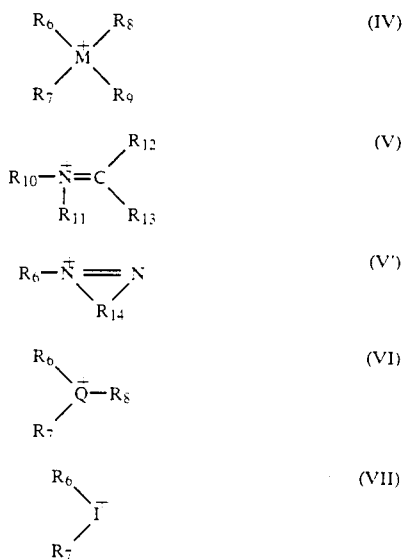

in which M represents N, P or As; Q represents S, O, Se, S=O or C; $R_6$, $R_7$, $R_8$ and $R_9$, which may be identical or different, are each a $C_{1-16}$ straight or branched alkyl radical, optionally substituted by one or more phenyl, hydroxy, halo, nitro, alkoxy or alkoxycarbonyl radicals, the alkoxy radicals having 1 to 4 carbon atoms; a $C_{2-12}$ straight or branched alkenyl radical; a $C_{6-10}$ aryl radical optionally bearing one or more of the following substituents, namely, $C_{1-4}$ alkyl, alkoxy, or alkoxycarbonyl radicals, the alkoxy radical having 1 to 4 carbon atoms, or halogen, with the proviso that two of said $R_6$ to $R_9$ radicals can together form a $C_{3-6}$ straight or branched alkylene, alkenylene or alkadienylene radical; $R_{10}$, $R_{11}$, $R_{12}$ and $R_{13}$, which may be identical or different, are each a $C_{1-4}$ straight or branched alkyl radical; the radicals $R_{12}$ and $R_{13}$ can together form a $C_{3-6}$ alkylene radical; the radicals $R_{11}$ and $R_{12}$ or $R_{11}$ and $R_{13}$ can together form an alkylene, alkenylene or alkadienylene radical containing 4 carbon atoms and forming, with the nitrogen atom from which they depend, a nitrogenous heterocycle; $R_{14}$ is a bivalent radical forming with the 2 nitrogen atoms a ring having 4 to 6 atoms, including one or more atoms of nitrogen, sulfur and/or oxygen, such cycle optionally having one or more radicals such as $R_6$ as substituents.

Among the "strong" or "intermediate" bases that can form the anion of said onium salts, exemplary are the following ions: $F^-$, $ClO_4^-$, $PF_6^-$, $BF_4^-$, $SnCl_6^-$, $SbCl_6^-$, $B(Ph)_4^-$, $PO_4^{3-}$, $HPO_4^{2-}$, $H_2PO_4^-$, $CH_3SO_3^-$, $Ph-SO_3^-$, $HSO_4^-$, $NO_3^-$, $SO_4^{2-}$, $Cl^-$, $Br^-$, $I^-$, $OH^-$, wherein Ph represents a phenyl radical, as well as the other anions corresponding to the definition of a "strong" or "intermediate" base by Pearson.

For purposes of ease of operation, such anions are advantageously $PO_4^{3-}$, $HPO_4^{2-}$, $H_2PO_4^-$, $CH_3SO_3$, $Ph-SO_3^-$, $NO_3^-$, $SO_4^{2-}$, $PF_6^-$, $Cl^{31}$, $Br^{31}$, $I^{31}$, with Ph being as defined above. Preferably the anions are $Br^-$ and $I^-$.

Exemplary of the organic cations corresponding to Formula (IV) are tetramethylammonium, triethylmethylammonium, tributylmethylammonium, trimethylpropylammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltriphenylammonium, buten-2-yltriethylammonium, N,N-dimethyltetramethyleneammonium, N,N-diethyltetramethyleneammonium, tetramethylphosphonium, tetrabutylphosphonium, ethyltrimethylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyltri(isopropyl)phosphonium, methyltri(n-propyl)phosphonium, methyltri(n-butyl)phosphonium, methyltri(2-methylpropyl)phosphonium, methyltricyclohexylphosphonium, methyltriphenylphosphonium, methyltribenzylphosphonium, methyltri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyltri(n-propyl)phosphonium, triethylpentylphosphonium, hexadecyltributylphosphonium, ethyltriphenylphosphonium, n-butyltri(n-propyl)phosphonium, butyltriphenylphosphonium, benzyltriphenylphosphonium, (beta-phenylethyl)dimethylphenylphosphonium, tetraphenylphosphonium, triphenyl(4-methylphenyl)phosphonium, tetrakis(hydroxymethyl)phosphonium and tetra-phenylarsonium.

Exemplary cations corresponding to formulae (V) and (V') are N-methylpyridinium, N-ethylpyridinium, N-hexadecylpyridinium, N-methylpicolinium and 1,2,4-triphenyltriazolium.

Exemplary organic cations corresponding to formula (VI) are trimethylsulfonium, triethylsulfonium, triphenylsulfonium, trimethylsulfoxonium, triphenylcarbenium and triethyloxonium.

Exemplary organic cations corresponding to formula (VII) are diphenyliodonium, 4,4'-dimethoxydiphenyliodonium (or the compounds described in *JACS*, 81, 342 (1958)), and diphenyliodonium-2-carboxylate.

Among the oniums used to carry out the present process, quaternary ammonium, quaternary phosphonium, sulfonium and iodonium ions are typically preferred. Particularly preferred are ammonium ions in which the four groups are identical alkyl radicals containing 4 or 5 carbon atoms.

As regards the selection of the cation, $Br^-$ or $I^-$ is preferred.

The onium can be soluble in the reaction medium; thus, the reaction is carried out in homogeneous medium.

It can also be in solid insoluble form; thus, the reaction is carried out in a biphasic solid/liquid medium.

This is of importance in the event that the onium is supported on an inorganic or polymeric resin.

Exemplary supported oniums include:
(i) tetrabutylammonium fluoride on silica gel;
(ii) tributylammonium chloride on a polymer marketed for example by the FLUKA company;
(iii) methyltributylphosphonium chloride on polystyrene, also marketed by the FLUKA company; and
(iv) benzyltrimethylammonium bromide on polymer.

The onium compound used in the process of the invention can be completely synthesized in the reaction medium or prepared in situ. In the latter case, the onium is prepared using a catalytic quantity of a quaternizable tertiary amine which, in the presence of the halogenated derivative of Formula (II), produces the desired ammonium. This amine is preferably triethylamine. Another technique for providing an onium comprises forming, in situ, the hydrohalide of the nonquaternizable tertiary amine by the halogenated derivative of formula (II) by reacting the latter with a catalytic quantity of a hydrohalic acid, preferably hydrobromic or hydrochloric acid. Such hydrohalic acid is preferably employed in the form of a concentrated solution thereof, or can equally as well be bubbled in gaseous form through the reaction medium.

In accordance with the process of the invention, the esterification reaction of the hydroxybenzoic acid is carried out in the presence of a nonquaternizable tertiary amine and optionally of an onium compound, the different reactants typically being used in the proportions indicated below.

The molar ratio between the number of carboxylic functions of the carboxylic acid and the number of halogen atoms of the halogenated derivatives preferably ranges from 0.9:1 to 2.0:1. It is preferably in the region 1.0:1.

When the onium is formed in situ from a quaternizable tertiary amine and a halogenated derivative, this must be used in a quantity exceeding the stoichiometric amount.

As regards the amount of nonquaternizable tertiary amine, this is determined by the manner in which it takes up the hydrohalic acid formed over the course of the reaction. It can thus range from the stoichiometric amount up to a stoichiometric excess of about 500% in the event that such amine is used as a solvent.

If the onium is formed in situ from the nonquaternizable tertiary amine and a hydrohalic acid, it is necessary to provide an excess with respect to the stoichiometry.

Concerning the onium, this is used in a catalytic quantity, i.e., a quantity such that the molar ratio between the onium and the carboxylic acid preferably ranges from 0.025:1 to 0.2:1.

As indicated above, the reaction can be carried out in the absence of any solvent, or else in the presence of an organic solvent.

The selection of solvent is determined as a function of its capability to solubilize the reactants, i.e., the carboxylic acid and the halogenated derivative. Furthermore, it must be inert under the reaction conditions.

It is not necessary, but is desirable, that the solvent selected should solubilize the nonquaternizable tertiary amine and the onium.

In a preferred embodiment of the invention, the nonquaternizable tertiary amine is used as the reaction solvent; N,N-diisopropylethylamine is preferably used.

Exemplary reaction solvents include the aliphatic or aromatic hydrocarbons, aliphatic or aromatic halogenated hydrocarbons, aliphatic esters, certain polar aprotic solvents such as linear or cyclic carboxamides, e.g., dimethylformamide, diethylformamide, and N-methylpyrrolidone; and aliphatic or aromatic nitriles such as acetonitrile, propionitrile or benzonitrile.

Exemplary aliphatic or aromatic hydrocarbons include hexane, heptane, octane, nonane, decane, cyclohexane, toluene and xylene.

Exemplary aliphatic or aromatic hydrocarbons include perchlorinated hydrocarbons, particularly carbon tetrachloride, tetrachloroethylene, hexachloroethane, hexachloropropene and hexachlorobutadiene; partially chlorinated hydrocarbons such as methylene chloride, dichloroethane, tetrachloroethane, trichloroethylene, 1-chlorobutane, 1,2-dichlorobutane, monochlorobenzene, 1,2-dichlorobenzene, 1,3-dichlorobenzene, 1,4-dichlorobenzene and mixtures of different chlorobenzenes; monobromobenzene and mixtures of monobromobenzene with one or more dibromobenzenes.

When the process of the invention is carried out in a solvent medium, the concentration of the hydroxybenzoic acid is not critical. It depends particularly on its solubility in the organic solvent used.

In one practical embodiment of the invention, the reactants can be mixed in any order.

In another preferred embodiment of the invention, a mixture of the carboxylic acid, nonquaternizable tertiary amine, optionally the onium and an organic solvent is prepared. Then the halogenated derivative is progressively added to the reaction medium.

The temperature at which the process of the invention is carried out is typically less than or equal to 120° C. This limitation is imposed strictly by economics, because the yield of the reaction decreases beyond this temperature. The lower temperature limit is about 50° C. This is not critical.

Preferably, the temperature ranges from 70° C. to 120° C.

The reaction pressure is not critical and is typically atmospheric pressure.

In order to attain the temperatures indicated above and avoid loss of solvent, it is preferable to carry out the reaction at autogenous pressure.

The reaction time varies over wide limits, for example from 15 minutes to 8 hours, but typically ranges from 1 to 2 hours.

Upon completion of the reaction, the carboxylic acid ester is separated from the reaction medium by conventional separation techniques such as extraction with a solvent, a solubilizer such as ethyl acetate or methylisobutylketone, and/or distillation.

If the esterification is carried out in an organic solvent, the reaction medium is diluted with water. The organic phase, which contains the formed ester and the excess of halogenated derivative, is then separated from the aqueous phase, which contains the hydrohalide of the nonquaternizable tertiary amine and possibly the onium.

The nonquaternizable tertiary amine can then be recovered by treating the aqueous phase with a basic solution, preferably caustic soda. It can then be recycled.

Another technique for recovering the ester formed comprises neutralizing the hydrohalide of the nonquaternizable tertiary amine with a base, preferably caustic soda.

The halogenated salt of the cation of the base, preferably NaCl or NaBr, is contained in the aqueous phase, which can be separated from the organic phase containing the ester formed, the halogenated derivative in the event of an excess thereof, and the nonquaternizable tertiary amine.

The ester can be purified by extraction with an organic solvent and/or by distillation.

It will be appreciated that the first technique for treating the reaction medium is preferred, because it permits the more direct production of a pure ester.

The process of the invention is well suited for the preparation of salicylic acid esters, particularly alkyl or alkenyl salicylates, for example methyl salicylate, ethyl salicylate, isopropyl salicylate, amyl or isoamyl salicylate, 2-methylpentyl salicylate, n-hexyl salicylate, 2-ethylbutyl salicylate, 2-ethylhexyl salicylate, 2-methyl-2-butenyl salicylate, and cis-3-hexenyl salicylate; substituted alkyl or alkenyl salicylates, for example glycol salicylate, monomethylamine salicylate and beta-isopropoxyethyl salicylate; optionally substituted cycloalkyl and cycloalkenyl salicylates, for example cyclohexyl salicylate, 2-isopropyl-cyclohexyl salicylate, 3,3,5-trimethylcyclohexyl salicylate and bornyl salicylate; and arylalkyl salicylates, for example benzyl salicylate.

The invention is equally well suited for the preparation of the esters of o-, m- or p-aminosalicylic acid. Particularly exemplary are menthyl o-amino and monosalicylate, menthyl p-amino and monosalicylate and allyl p-amino and monosalicylate.

The process of the invention is equally suitable for the preparation of esters of p-hydroxybenzoic acid. Particularly exemplary thereof are methyl p-hydroxybenzoate and propyl p-hydroxybenzoate.

The process of the present invention is especially advantageous in that it permits hydroxybenzoic acid esters to be prepared with good conversions of the starting acid and with good selectivity with respect to the O-alkylation that is known to occur in the processes of the prior art.

In order to further illustrate the present invention and the advantages thereof, the following specific examples are given, it being understood that same are intended only as illustrative and in nowise limitative.

In said examples to follow, the abbreviations have the following significance:

$$TT_H = \frac{\text{number of moles of halogen derivative transformed}}{\text{number of moles of halogen derivative introduced}} \%$$

$$TT_A = \frac{\text{number of moles of hydroxybenzoic acid transformed}}{\text{number of moles of hydroxybenzoic acid introduced}} \%$$

$$RR_H = \frac{\text{number of moles of hydroxybenzoic acid ester formed}}{\text{number of moles of halogenated derivative introduced}} \%$$

$$RR_A = \frac{\text{number of moles of hydroxybenzoic acid ester transformed}}{\text{number of moles of hydroxybenzoic acid introduced}} \%$$

$$RT_H = \frac{\text{number of moles of hydroxybenzoic acid ester formed}}{\text{number of moles of halogenated derivative transformed}} \%$$

$$RT_A = \frac{\text{number of moles of hydroxybenzoic acid ester formed}}{\text{number of moles of hydroxybenzoic acid transformed}} \%$$

Examples 1 to 40 illustrate the preparation of benzyl salicylate.

Examples 41 to 43 illustrate the preparation of isopropyl and cyclohexyl salicylate.

Example 44 illustrates the preparation of benzyl p-hydroxybenzoate.

EXAMPLE 1

1.1 g (8 mM) of salicylic acid, 1.0 g (8 mM) of benzyl chloride and 1.03 g (8 mM) of N,diisopropylethylamine (DIPEA) were introduced into a 30-ml glass reactor provided with a stirrer, a thermostat, a refrigerant and equipped with a heating system.

The reaction mixture was stirred and brought to a temperature of 70° C. The total time of heating was 5 hours. Upon completion of the reaction and after cooling, 8 ml of 1N aqueous caustic soda solution were added, the organic products were extracted with 3×5 ml of ethyl acetate, and the benzyl salicylate was determined by gas-phase chromatography (GPC).

The results obtained are reported in Table I:

TABLE I

| Example | Non-quaternizable Tertiary Amine | Temperature °C. | $TT_H$ Benzyl Chloride | $RR_H$ Benzyl Salicylate |
|---|---|---|---|---|
| 1 | EA | 70 | 84.6 | 81.9 |

EXAMPLE 2

11 g (80 mM) of salicylic acid and 10.3 g (80 mM) of N,N-diisopropylethylamine were introduced into a 150-ml reactor equipped as in Example 1, additionally provided with a flow funnel.

The reaction mixture was brought to 70° C. and 10.1 g (80 mM) of benzyl chloride were introduced over 20 minutes. The reaction mixture was maintained at 100° C. with stirring. The total heating time was 5 hours. After cooling, the reaction mass was treated as in Example 1 and the benzyl salicylate was determined by GPC.

The results obtained are reported in Table II:

TABLE II

| Example | Non-quaternizable Tertiary Amine | Temperature °C. | $TT_H$ Benzyl Chloride | $RR_H$ Benzyl Salicylate |
|---|---|---|---|---|
| 2 | DIPEA | 100 | 93.9 | 85.9 |

EXAMPLES 3 TO 7

Influence of the Reaction Temperature

The procedure of Example 1 was repeated, using 1.1 g (8 mM) of salicylic acid, 1.0 g (8 mM) of benzyl chloride and 1.03 g (8 mM) of N,N-diisopropylethylamine.

The reaction was carried out at differing temperatures, the reaction period always being the same at 5 hours.

The results obtained are reported in Table III:

TABLE III

| Example | Non-quaternizable Tertiary Amine | Temperature °C. | $TT_H$ Benzyl Chloride | $RR_H$ Benzyl Salicylate | $RT_H$ Benzyl Salicylate |
|---|---|---|---|---|---|
| 1 | DIPEA | 70 | 84.6 | 81.9 | 96.8 |
| 3 | DIPEA | 80 | 89.9 | 81.4 | 90.5 |
| 4 | DIPEA | 90 | 93.8 | 85.5 | 91.1 |
| 5 | DIPEA | 100 | 90.9 | 87.7 | 96.5 |
| 6 | DIPEA | 110 | 92.4 | 78.2 | 84.6 |
| 7 | DIPEA | 120 | 94.7 | 73.4 | 77.5 |

It will be seen from the above Table that the optimum temperature corresponding to the best reaction selectivity is around 100° C. and that at temperatures varying therefrom a reduction in the selectivity to the ester produced was observed.

EXAMPLES 8 TO 13

Influence of the Reaction Time

The procedure of Example 1 was repeated using 1.1 g (8 mM) of salicylic acid, 1.0 g (8 mM) of benzyl chloride and 1.03 g (8 mM) of N,N-diisopropylethylamine.

The reaction was carried out at 100° C. over varying times as reported in the following Table IV:

TABLE IV

| Example | Time (h) | Temperature °C. | $TT_H$ Benzyl Chloride | $RR_H$ Benzyl Salicylate |
|---|---|---|---|---|
| 8 | 0.5 | 100 | 84.6 | 67.0 |
| 9 | 1 | 100 | 90.9 | 67.3 |
| 10 | 2 | 100 | 93.7 | 70.7 |
| 11 | 3 | 100 | 93.3 | 67.1 |

It will be appreciated that the reaction was rapid and that prolonged reaction times provided no advantage.

EXAMPLES 14 TO 15

Influence of the Quantity of Non-quaternizable Amine

The procedure of Example 1 was repeated using 1.1 g (8 mM) of salicylic acid, 1.0 g (8 mM) of benzyl chloride and Xg of N,N-diisopropylethylamine.

The quantity of DIPEA was determined in such manner that the molar ratios between the DIPEA and the salicylic acid were as set forth in the following Table V.

The reaction temperature was 70° C.

The total time of heating was 5 hours.

TABLE V

| Example | Molar Ratio DIPEA: Salicylic Acid | Temperature °C. | $TT_H$ Benzyl Chloride | $RR_H$ Benzyl Salicylate | $RT_H$ Benzyl Salicylate |
|---|---|---|---|---|---|
| 14 | 2.9 | 70 | 84.3 | 79.8 | 94.6 |
| 15 | 2.4 | 70 | 83.5 | 83.4 | 99.8 |
| 1 | 1.0 | 70 | 84.6 | 81.9 | 96.8 |

The quantity of amine used was not critical, since it was at least equal to the stoichiometric amount.

EXAMPLES 16 TO 20

Influence of the Nature of the Non-quaternizable Tertiary Amine Used

The procedure of Example 1 was repeated using 1.1 g (8 mM) of salicylic acid, 1.0 g (8 mM) of benzyl chloride and Xg (24 mM) of a nonquaternizable tertiary amine.

The nature of the amine used is reported in the following Table VI.

The reaction temperature was 100° C.

The heating time was 5 hours.

TABLE VI

| Example | Non-quaternizable Tertiary Amine | Temperature °C. | $TT_H$ Benzyl Chloride | $RR_H$ Benzyl Salicylate | $RT_H$ Benzyl Silicylate |
|---|---|---|---|---|---|
| 16 | N,N-diisopropyl n-propylamine | 100 | 71.3 | 68.3 | 95.8 |
| 17 | N,N-diisobutyl-ethylamine | 100 | 24.6 | 24.6 | 100 |
| 18 | N,N-diisopropyl-allylamine | 100 | 61.7 | 50.9 | 82.5 |
| 19 | N,N-dicylohexyl-ethylamine | 100 | 54.7 | 50.0 | 91.4 |
| 20* | N,N-diphenyl-ethylamine | 100 | 4.0 | 3.5 | 87.5 |

Examination of Table VI indicates the following:

(i) the presence of isopropyl radicals in the structure of the tertiary amine is favorable, and (ii) the presence of two phenyl radicals in the structure of the tertiary amine appears to be critical.

EXAMPLE 21

A comparative test was carried out using a quaternizable amine.

The procedure of Example 1 was repeated using 1.1 g (8 mM) of salicylic acid, 1.0 g (8.0 mM) of benzyl chloride and 2.3 g (23 mM) of triethylamine.

The reaction temperature was 70° C.

The heating time was 5 hours.

Under these conditions, the rate of transformation of the benzyl chloride was 100%, but the yield ($RR_H$) of benzyl salicylate was only 61.1%, which corresponds to a yield ($RT_H$) of 61.1%.

Thus, a substantial decrease in selectivity was observed.

EXAMPLES 22 TO 28

Influence of the Presence and Nature of a Solvent

The esterification reaction of salicylic acid was carried out in the absence of solvent (Example 22) and in a series of tests the nature of the solvent was varied (Examples 23 to 28).

The procedure of Example 1 was repeated using 1.1 g (8 mM) of salicylic acid, 1.0 g (8 mM) of benzyl chloride and 1.03 g (8 mM) of N,N-diisopropylethylamine, and 5 ml of solvent.

The reaction mixture was stirred and brought to a temperature of 70° C.

The heating time was 5 hours.

The different results obtained are reported in Table VII:

TABLE VII

| Example | Solvent | Temperature °C. | $TT_H$ Benzyl Chloride | $RR_H$ Benzyl Salicylate |
|---|---|---|---|---|
| 22 | — | 70 | 84.6 | 81.9 |
| 23 | heptane | 70 | 75.9 | 75.8 |
| 24 | 1,2-dichloroethane | 70 | 34.4 | 32.0 |
| 25 | acetonitrile | 70 | 66.9 | 66.4 |
| 26 | dimethylformamide | 70 | 85.9 | 85.0 |
| 27* | diisopropylether | 70 | 70.1 | 21.5 |
| 28* | ethanol | 70 | 38.5 | 27.4 |

The use of organic solvents admixed with N,N-diisopropylethylamine resulted in a decrease in the reaction performance, likely due to problems of solubility and miscibility of the liquids among themselves.

EXAMPLES 29 TO 37

Influence of the Presence of an Onium Salt

The esterification reaction of salicylic acid was carried out in the absence of an onium salt (Example 29) and in a first series of tests the nature of the onium salt was varied (Examples 30 to 37).

The procedure of Example 1 was repeated using 1.1 g (8 mM) of salicylic acid, 1.0 g (8 mM) of benzyl chloride and 1.03 g ( 8 mM) of N,N-diisopropylethylamine, and $\times$ g (0.8 mM) of an onium salt.

The nature of the onium salt is indicated in Table VIII.

The reaction temperature was 50° C.

The total heating was 1 hour.

TABLE VIII

| Example | Onium Salt | Temperature °C. | $TT_H$ Benzyl Chloride | $RR_H$ Benzyl Salicylate |
|---|---|---|---|---|
| 29 | — | 50 | 7.2 | 7.2 |
| 30 | $(Ph)_4 P^+ Cl^-$ | 50 | 28.3 | 27.9 |
| 31 | $(Ph)_4 P^+ I^-$ | 50 | 59.9 | 45.3 |
| 32 | $(Bu)_4 N^+ Br^-$ | 50 | 46.0 | 54.8 |
| 33 | $Ph(Me)_3 N^+ Br^-$ | 50 | 38.4 | 26.2 |
| 34 | $Ph(Me)_3 N^+ I^-$ | 50 | 55.2 | 50.9 |
| 35 | $(Me)_3 S^+ O I^-$ | 50 | 36.8 | 33.4 |
| 36 | $(Et)_4 N^+ I^-$ | 50 | 47.5 | 43.0 |
| 37 | $(Bu)_4 P^+ Cl^-$ | 50 | 32.6 | 25.0 |

In all cases there was an increase in the yield of benzyl salicylate.

EXAMPLE 38

54.6 g (395 mM) of salicylic acid and 51.60 g (365 mM) of N,N-diisopropylethylamine were introduced into a reactor as described in Example 2.

The reaction mixture was brought to 100° C. and 46.2 g (365 mM) of benzyl chloride were introduced over 50 minutes. The reaction mixture was maintained at 100° C. for 70 minutes with stirring. After cooling to 65° C., 110 ml of methylisobutylketone and 100 ml of water were added and the organic and aqueous phases were separated.

The organic phase was washed three times with water and the different organic compounds were determined: 79.3 g (348 mM) of benzyl salicylate, 2.4 g (19 mM) of benzyl chloride and 0.2 g of N,N-diisopropylethylamine.

The yield of benzyl salicylate was determined as 95.5% and the degree of conversion of benzyl chloride was 94.8%.

The aqueous phase, which contained N,N-diisopropylethylamine hydrochloride, was treated with 13 ml of a 10N solution of caustic soda (pH=13). This produced two phases, an organic phase containing 47.6 g of N,N-diisopropylethylamine, i.e., 90% of the weight added, and the aqueous phase containing sodium chloride which was subjected to three extractions with methylisobutylketone.

1.57 g of N,N-diisopropylethylamine was recovered and 5.52 g of salicylic acid were determined, which corresponded to a degree of conversion of the latter of 87.2%. Therefore, the amine was recovered at 93% and having a purity of more than 98%.

EXAMPLES 39 AND 40

In these two examples of the preparation of benzyl salicylate, an excess of salicylic acid was used.

The N,N-diisopropylethylamine and the benzyl chloride were introduced into a reactor such as described in Example 2 and the salicylic acid was introduced into the reaction mixture over 20 minutes with stirring. The quantities used are reported in Table IX. The reaction temperature was 55° C. The total time of heating was 5 hours. At this temperature, 200 ml of water were added and the organic phase (phase I) and the aqueous phase were separated. The organic phase was washed with 2×10 ml of water; all of the aqueous phases were combined and washed with 3×30 ml of methylene chloride (phase II); and the constituents of the organic phases I and II were determined by GPC.

TABLE IX

| Example | Quantity of Salicylic acid (g) | Quantity of Benzyl Chloride (g) | Molar Ratio SA:BC | Quantity of DIPEA | Temperature °C. | $TT_H$ Benzyl Chloride | $RR_H$ Benzyl Salicylate |
|---|---|---|---|---|---|---|---|
| 39 | 37.4 | 21.64 | 1.6 | 34.76 | 55 | 98.7 | 99 |
| 40 | 22.85 | 15.10 | 1.4 | 21.87 | 55 | 98.3 | 99 |

EXAMPLES 41 AND 42

Influence of the Halogenated Derivative

In the following Examples, different salicylic acid esters were prepared.

Accordingly, different halogenated derivatives, the nature of which is reported in Table X, were used. The procedure of Example 1 was repeated using 1.1 g (8 mM) of salicylic acid, ×g (8 mM) of halogenated derivative and 1.03 g (8 mM) of N,N-diisopropylethylamine. The reaction temperature was 100° C. The total heating time was 5 hours.

TABLE X

| Example | Halogenated Derivative | Temperature °C. | $TT_A$ Salicylic Acid | $TT_H$ Halogenated Derivative | $SS_H$ Salicylic Ester |
|---|---|---|---|---|---|
| 41 | Isopropyl bormide | 100 | 55 | 51 | 50 |
| 42 | Bromo-cyclohexane | 100 | 58.8 | 56 | 53 |

EXAMPLE 43

In this Example, isopropyl salicylate was prepared.

22.11 g (171 mM) of N,N-diisopropylethylamine and 21.03 g (171 mM) of isopropyl bromide were introduced into a reactor as described in Example 2. 23.6 g (171 mM) of salicylic acid were progressively added to the stirred reaction mixture. The reaction mixture, maintained stirred, was brought progressively to 100° C. The total heating time was 5 hours, 30 minutes. The reaction mass was then treated as in Example 39 and all of the aqueous phases were combined and washed with 2×50 ml of methylene chloride.

The different constituents in the combined organic phases were determined by GPC. Under these conditions, the rates of transformation of isopropyl bromide ($TT_H$) and salicylic acid ($TT_A$) were both equal to 93%. The yield of isopropyl salicylate ($RR_H$) was 95.5%.

EXAMPLE 44

In this Example, the benzyl ester of another hydroxybenzoic acid, i.e., 4-hydroxybenzoic acid, was prepared.

The procedure of Example 1 was repeated using 1.1 g (8 mM) of 4-hydroxybenzoic acid, 1.0 g (8 mM) of benzyl chloride and 1.03 g (8 mM) of N,N-diisopropylethylamine. The reaction temperature was 70° C. The total heating time was 5 hours.

TABLE XI

| Example | Hydroxybenzoic Acid | Temperature °C. | $TT_H$ Benzyl Chloride | $RR_H$ Benzyl p-hydroxybenzoate |
|---|---|---|---|---|
| 44 | 4-hydroxybenzoic acid | 70 | 51.8 | 47 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an ester of a hydroxybenzoic acid, comprising reacting such hydroxybenzoic acid with a halocarbon, in essentially homogeneous liquid phase in the presence of a catalytically effective amount of a nonquaternizable tertiary amine.

2. The process as defined by claim 1, said halocarbon comprising a halogenated derivative of an aliphatic, cycloaliphatic, cyclo- or arylaliphatic hydrocarbon.

3. The process as defined by claim 2, said hydroxybenzoic acid having the following formula (I):

$$\begin{array}{c} \text{COOH} \\ | \\ R_0 - \bigcirc - R_2 \\ | \\ R_1 \end{array} \quad (I)$$

in which $R_0$ is a hydroxy group; $R_1$ and $R_2$, which may be identical or different, are each a hydrogen atom, an —OH group, a straight or branched $C_{1-6}$ alkyl radical, an alkoxy radical $R_3$—O—, wherein $R_3$ is a $C_{1-6}$ straight or branched alkyl radical, a —COOH group, a —CHO group, a $C_{2-6}$ acyl radical, a group —COOR'$_3$ wherein R'$_3$ is a straight or branched $C_{1-4}$ alkyl radical, an —NO$_2$ group, a halogen atom, or a —CF$_3$ group.

4. The process as defined by claim 3, wherein formula (I), $R_1$ and $R_2$, which may be identical or different, are each a hydrogen atom, a hydroxy group, or a straight or branched $C_{1-6}$ alkoxy radical.

5. The process as defined by claim 3, wherein formula (I), $R_1$ and $R_2$, which may be identical or different, are each hydrogen, hydroxy, methyl or methoxy.

6. The process as defined by claim 2, said hydroxybenzoic acid comprising salicylic acid or parahydroxybenzoic acid.

7. The process as defined by claim 2, said halogenated derivative having the following formula (II):

$$R_4 - X \quad (II)$$

in which X is a halogen atom in other than a vinylic or alkynylic position and $R_4$ is an optionally substituted acyclic saturated or unsaturated straight or branched aliphatic radical, cycloaliphatic saturated or unsaturated monocyclic or polycyclic radical; or straight or branched saturated or unsaturated cyclo- or arylaliphatic radical.

8. The process as defined in claim 7, wherein formula (II), $R_4$ is (1) a straight or branched alkyl, alkenyl, alkadienyl or alkynyl radical, the hydrocarbon chain thereof optionally being interrupted by one of the following groups:

$$-O-, -CO-, -COO-, -\underset{\underset{R_5}{|}}{N}-, -CO-\underset{\underset{R_5}{|}}{N}-$$

wherein $R_5$ is a hydrogen atom, a $C_{1-4}$ alkyl radical or a cyclohexyl or phenyl radical, with the proviso that $R_5$ is a hydrogen atom in the event that the nitrogen atom is not quaternizable and/or bears one of the following Y substituents: an —OH group, a —COOH group, an —NO$_2$ group, a —C≡N group, a nonquaternizable or N-protected amino group, a halogen atom, or a —CF$_3$ group; (2) a cycloalkyl or cycloalkenyl radical optionally bearing one or more of the following: the above Y substituents and the following Z substituents: a C$_{1-4}$ straight or branched alkyl radical, a C$_{1-4}$ straight or branched alkoxy radical or a radical of the formulae:

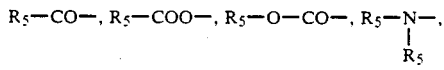

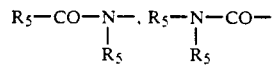

wherein R$_5$ is as defined above, with the proviso that said radicals can be polycyclic and bridged; or (3) a saturated or unsaturated, straight or branched acyclic aliphatic radical as indicated under (1), bearing a cyclic substituent, the aliphatic acyclic radical being attached to the ring via a valence bond or one of the following groups:

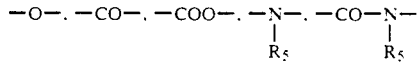

in which R$_5$ is as defined above.

9. The process as defined by claim 8, wherein formula (II), R$_4$ is (a) a cyclo aliphatic mono- or polycyclic radical as indicated in (2); (b) a phenyl, tolyl or xylyl radical, optionally bearing one or more Y or Z substituents; (c) a saturated, unsaturated or aromatic monocyclic heterocyclic radical containing one or more oxygen, nitrogen or sulfur heteroatoms and containing 4 to 6 atoms in the ring heterocycle, such radical optionally bearing one or more Y or Z substituents; (d) a radical comprising a chain of 2 to 4 of the following: groups (a), (b) and (c), bonded to one another via the following: a valence bond, one of the following groups:

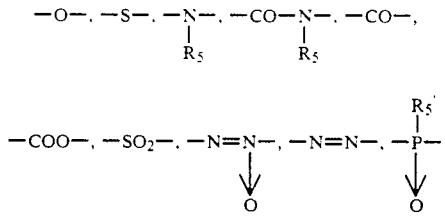

or at least one C$_{1-4}$ alkylene or alkylidene radical, wherein R$_5$ and R$_5'$ are each a hydrogen atom, a C$_{1-4}$ alkyl radical or a cyclohexyl or phenyl radical, with the proviso that R$_5$ can be a hydrogen atom in the event that the nitrogen atom does not quaternize; or (e) an aromatic radical comprising 2 or 3 of the following: aromatic carbocyclic and heterocyclic ring members defining an orthocondensed system.

10. The process as defined by claim 9, wherein formula (II), R$_4$ is a C$_{1-8}$ straight or branched alkyl radical, a C$_{2-8}$ straight or branched alkenyl radical containing an ethylenic double bond beta to the X group, a cyclohexyl radical optionally bearing a straight or branched C$_{1-4}$ alkyl substituent, or an aralkyl radical having the formula

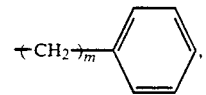

in which m is an integer ranging from 1 to 4.

11. The process as defined by claim 10, said halogenated derivative comprising allyl bromide, allyl chloride, benzyl bromide, benzyl chloride, isopropyl bromide, crotyl chloride, 1-chloro-2-butene, or cyclohexyl bromide.

12. The process as defined by claim 2, said nonquaternizable tertiary amine comprising a tertiary amine in which at least one of the radicals borne by the nitrogen atom is a branched aliphatic radical.

13. The process as defined by claim 12, said nonquaternizable tertiary amine having the following formula (III):

in which R', R'' and R''', which may be identical or different, are each a C$_{1-12}$ straight or branched saturated or unsaturated aliphatic radical, a C$_{5-7}$ saturated or unsaturated cycloaliphatic radical, or a phenyl radical, with the proviso that at least one of the radicals R', R'' and R''' is a branched aliphatic radical, and at most one of the radicals R', R'' and R''' is a phenyl radical.

14. The process as defined by claim 13, wherein formula (III), at least one of the radicals R', R'' and R''' is a branched aliphatic radical branched on the carbon atom in alpha position with respect to the nitrogen atom.

15. The process as defined by claim 12, said nonquaternizable tertiary amine having a pKa greater than 9.0.

16. The process as defined by claim 12, said nonquaternizable tertiary amine comprising diisopropylmethylamine, N,N-diisopropylethylamine, N,N-diisopropyl-n-propylamine, N,N-diisopropylpropylamine, N,N-di(sec-butyl)ethylamine, N,N,N-triisopropylamine, N,N-diisopropylallylamine, N,N-di(sec-butyl)allylamine, N,N-dicyclohexylethylamine or N,N-diisopropylaminoethanol.

17. The process as defined by claim 2, carried out in the further presence of an onium compound having one of the following general formulae:

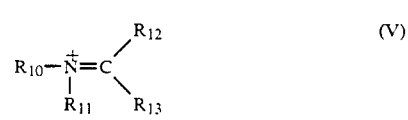

-continued

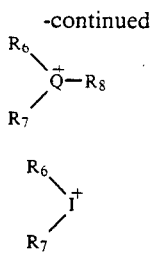

in which M is N, P or As; Q is S, O, Se, S=O or C; $R_6$, $R_7$, $R_8$ and $R_9$, which may be identical or different, are each a $C_{1-16}$ straight or branched alkyl radical, optionally substituted by one or more phenyl, hydroxy, halo, nitro, alkoxy or alkoxycarbonyl radicals, the alkoxy radicals having 1 to 4 carbon atoms; a $C_{2-12}$ straight or branched alkenyl radical; a $C_{6-10}$ aryl radical optionally substituted by one or more $C_{1-4}$ alkyl, alkoxy or alkoxycarbonyl substituents, the alkoxy radical having 1 to 4 carbon atoms, or halogen substituents, with the proviso that two of said $R_6$ to $R_9$ radicals may together form a $C_{3-6}$ straight or branched alkylene, alkenylene or alkadienylene radical; $R_{10}$, $R_{11}$, $R_{12}$ and $R_{13}$, which may be identical or different, are each a $C_{1-4}$ straight or branched alkyl radical, with the proviso that radicals $R_{12}$ and $R_{13}$ may together form a $C_{3-6}$ alkylene radical and the radicals $R_{11}$ and $R_{12}$ or $R_{11}$ and $R_{13}$ may together form an alkylene, alkenylene or alkadienylene radical containing 4 carbon atoms and defining with the nitrogen atom from which they depend a nitrogenous heterocycle; and $R_{14}$ is a divalent radical forming with the 2 nitrogen atoms from which it depends a ring member having 4 to 6 atoms including one or more atoms of the following nitrogen, sulfur or oxygen, or a substituted such heterocycle.

18. The process as defined by claim 17, the anion of said onium salt comprising $F^-$, $ClO_4^-$, $PF_6^-$, $BF_4^-$, $SnCl_6^-$, $SbCl_6^-$, $B(Ph)_4^-$, $PO_4^{3-}$, $HPO_4^{2-}$, $H_2PO_4^-$, $CH_3SO_3^-$, $Ph-SO_3^-$, $HSO_4^-$, $NO_3^-$, $SO_4^{2-}$, $Cl^-$, $Br^-$, $I^{31}$, $OH^-$, wherein Ph is a phenyl radical.

19. The process as defined by claim 17, said compound comprising a quaternary ammonium ion, a quaternary phosphonium ion, a sulfonium ion or an iodonium ion.

20. The process as defined by claim 2, wherein the molar ratio between the number of carboxylic functions of the hydroxybenzoic acid and the number of halogen atoms comprising the halogenated derivative ranges from 0.9:1 to 2.0:1.

21. The process as defined by claim 2, wherein the nonquaternizable tertiary amine is present in a total amount which ranges from the stoichiometric amount up to a stoichiometric excess of 500%.

22. The process as defined by claim 17, wherein the molar ratio of onium compound: hydroxybenzoic acid ranges from 0.025:1 to 0.2:1.

23. The process as defined by claim 2, carried out in a solvent comprising an aliphatic or aromatic hydrocarbon, halogenated aliphatic or aromatic hydrocarbon, aprotic polar solvent or a nonquaternizable tertiary amine.

24. The process as defined by claim 2, carried out at a reaction temperature ranging from 70° C. to 120° C.

25. The process as defined by claim 2, wherein the halogenated derivative is added progressively to the reaction medium comprising the hydroxybenzoic acid and the nonquaternizable tertiary amine.

* * * * *